(12) United States Patent
Hnat

(10) Patent No.: US 12,403,091 B2
(45) Date of Patent: *Sep. 2, 2025

(54) DELIVERY SYSTEM

(71) Applicant: SMARTECH TOPICAL, INC., Santee, CA (US)

(72) Inventor: Thomas Hnat, Santee, CA (US)

(73) Assignee: SMARTECH TOPICAL, INC., Santee, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/205,995

(22) Filed: Jun. 5, 2023

(65) Prior Publication Data

US 2023/0310318 A1    Oct. 5, 2023

Related U.S. Application Data

(62) Division of application No. 16/087,989, filed as application No. PCT/US2017/025373 on Mar. 31, 2017, now Pat. No. 11,666,531.

(60) Provisional application No. 62/316,064, filed on Mar. 31, 2016.

(51) Int. Cl.

| | | |
|---|---|---|
| A61K 9/06 | (2006.01) |
| A61K 9/00 | (2006.01) |
| A61K 31/167 | (2006.01) |
| A61K 31/192 | (2006.01) |
| A61K 31/196 | (2006.01) |
| A61K 31/216 | (2006.01) |
| A61K 31/245 | (2006.01) |
| A61K 31/352 | (2006.01) |
| A61K 31/385 | (2006.01) |
| A61K 31/522 | (2006.01) |
| A61K 31/714 | (2006.01) |
| A61K 45/06 | (2006.01) |
| A61K 47/10 | (2017.01) |
| A61K 47/14 | (2017.01) |
| A61K 47/44 | (2017.01) |

(52) U.S. Cl.
CPC .............. *A61K 9/06* (2013.01); *A61K 9/0014* (2013.01); *A61K 31/167* (2013.01); *A61K 31/192* (2013.01); *A61K 31/196* (2013.01); *A61K 31/216* (2013.01); *A61K 31/245* (2013.01); *A61K 31/352* (2013.01); *A61K 31/385* (2013.01); *A61K 31/522* (2013.01); *A61K 31/714* (2013.01); *A61K 45/06* (2013.01); *A61K 47/10* (2013.01); *A61K 47/14* (2013.01); *A61K 47/44* (2013.01)

(58) Field of Classification Search
CPC ........ A61K 9/06; A61K 9/0014; A61K 45/06; A61K 47/10; A61K 47/14; A61K 47/44; A61K 31/167; A61K 31/192; A61K 31/196; A61K 31/216; A61K 31/245; A61K 31/352; A61K 31/385; A61K 31/522; A61K 31/714; A61K 47/34

See application file for complete search history.

(56) References Cited

U.S. PATENT DOCUMENTS

| | | | |
|---|---|---|---|
| 7,622,138 B2 | 11/2009 | Murthy | |
| 8,980,290 B2 * | 3/2015 | Carrara | A61K 31/56 514/534 |
| 9,012,402 B1 | 4/2015 | Blanchard | |
| 10,702,469 B2 | 7/2020 | Patel | |
| 11,666,531 B2 | 6/2023 | Hnat | |
| 2008/0319092 A1 * | 12/2008 | Singh | A61K 47/16 514/784 |
| 2010/0120918 A1 * | 5/2010 | Patel | A61P 29/00 514/567 |
| 2011/0300083 A1 | 12/2011 | Yontz et al. | |
| 2012/0213842 A1 | 8/2012 | Birbara | |
| 2012/0244090 A1 | 9/2012 | Martinetti et al. | |
| 2014/0088195 A1 * | 3/2014 | Buyuktimkin | A61P 25/06 514/570 |
| 2016/0022603 A1 | 1/2016 | Spakevicius et al. | |
| 2016/0101077 A1 | 4/2016 | Bannister et al. | |
| 2016/0213784 A1 | 7/2016 | Kisak et al. | |
| 2018/0250242 A1 * | 9/2018 | Spakevicius | A61P 29/02 |

FOREIGN PATENT DOCUMENTS

| | | | |
|---|---|---|---|
| CN | 102652730 B | 4/2014 |
| JP | S63225312 A2 | 9/1988 |
| JP | H04124134 A2 | 4/1992 |

(Continued)

OTHER PUBLICATIONS

Office Action issued by the JPO in Japanese Patent Application No. 2019-502529 dated Feb. 24, 2021—incl Engl lang transl (20 pages total).

(Continued)

*Primary Examiner* — Snigdha Maewall
(74) *Attorney, Agent, or Firm* — Michael A. Whittaker

(57) ABSTRACT

In accordance with the present disclosure, there are provided formulations comprising:

(a) at least one active agent;
(b) an oil, and optionally a thickener therefor;
(c) an organic solvent, and a thickener therefor; and
(d) an oil and/or solvent soluble skin penetration enhancer;

wherein:
said formulation comprises <10 wt % water; and
said formulation optionally forms a thixotropic thinning gel.

Also provided are gels comprising oil and organic solvent, methods for preparing same and methods for the topical delivery of an active agent to a subject in need thereof.

13 Claims, No Drawings

(56) References Cited

FOREIGN PATENT DOCUMENTS

| | | | |
|---|---|---|---|
| JP | 2006-265153 | A2 | 10/2006 |
| JP | 2014-513132 | A2 | 5/2014 |
| JP | 2015-164950 | A2 | 9/2015 |
| JP | 2016-502530 | A2 | 1/2016 |
| WO | 2009047785 | A2 | 4/2009 |
| WO | 2013088375 | A1 | 6/2013 |
| WO | 2017173269 | A1 | 10/2017 |

OTHER PUBLICATIONS

International Search Report and Written Opinion mailed Jun. 22, 2017, for International Application No. PCT/US2017/025373 (6 pages).
The Extended European Search Report issued in EP 17776775 dated Nov. 11, 2019 (7 pages).

\* cited by examiner

DELIVERY SYSTEM

CROSS-REFERENCE TO RELATED APPLICATIONS

The present application is a divisional of U.S. patent application Ser. No. 16/087,989, filed Sep. 24, 2018, now U.S. Pat. No. 11,666,531, which is the United States National Phase application of PCT/US21017/025373, filed Mar. 31, 2017, which claims the benefit of priority to U.S. Provisional Application No. 62/316,064, filed Mar. 31, 2016, each of which is incorporated herein by reference.

FIELD

The present disclosure relates to formulations for topical application of active(s) and methods for the use (e.g., for the human and/or veterinary use) of such formulations for the transdermal delivery of active(s) via the skin and/or nails

BACKGROUND

The information provided herein and references cited are provided solely to assist the understanding of the reader, and does not constitute an admission that any of the references or information is prior art to the present disclosure.

SUMMARY

Delivering drugs and other components through the skin and/or nails minimizes side effects and distress to the gastrointestinal system and can minimize liver toxicity. Targeted localized delivery can also improve response time and minimize the dosage needed for effective relief. An effective topical delivery system could potentially replace oral delivery of some drugs.

Indeed, there is the potential that localized, topical delivery of an active such as an opioid may allow for the use of lower doses of the active to achieve the desired therapeutic effect (e.g., pain relief). An additional benefit would be the lowering of the opioid drug addiction problem, reducing withdrawal, and relieving constipation—all of which are significant side effects of oral administration of opioids.

In accordance with the present disclosure, minimal or no water systems are also contemplated, where water activity is used to preserve the product and the need for chemical preservatives is minimal or eliminated in both the solvent and oil phases. Stable oils (or oil stabilizers such as mixed tocopherols and ascorbyl palmitate, BHA or BHT) can be chosen to minimize oxidative degradation. High concentrations of actives (for example: naproxen (15%), acetaminophen (30%), ibuprofen (25%)) can surprisingly be solubilized and delivered topically. The ability to solubilize high concentrations of actives allows for the lowering of the total dosage needed to achieve efficacy. The ability to solubilize high concentrations of actives also results in a minimal amount of excipients being delivered per dose. The availability of only low concentrations of an active in a product means that larger amounts of excipients are required in order to deliver the correct dosage. The targeted, localized delivery of high concentrations of actives in a product (employing a lower overall dosage compared to the effective oral dose of the same active) can be applied to the delivery of multi-drug and multi-component combinations. Different drug categories (or combinations of different drug categories not expressly listed herein) can readily be achieved especially when the overall active oral dosage is less than 30 mg.

In accordance with an aspect of the present disclosure, there are provided formulations comprising:
(a) at least one active agent;
(b) an oil, and optionally a thickener therefor;
(c) an organic solvent, and a thickener therefor; and
(d) an oil and/or solvent soluble skin penetration enhancer;
wherein:
said formulation comprises <10 wt % water; and
said formulation optionally forms a thixotropic thinning gel.

The quantity employed for each element set forth above can vary widely; see, for example, the ranges set forth in Table 1. As readily recognized by those of skill in the art, the concentrations of the "active" can vary widely depending on the class of active compound employed. Moreover, any one of the ranges set forth herein can be combined with any of the other ranges set forth herein.

TABLE 1

Formulation Ranges*

| | Active | Oil Phase | Oil Phase Thickener | Organic Solvent Phase | Organic Solvent Phase Thickener |
|---|---|---|---|---|---|
| Broad Range | 0.001-40 | 15-50 | 0.5-15 | 5.0-60.0 | 2.0-20.0 |
| Preferred Range | 0.01-30 | 20-40 | 1.0-10 | 15.0-50.0 | 4.0-20.0 |
| Most Preferred Range | 10-25 | 30-40 | 2.0-5 | 20-40.0 | 6.0-12 |

*All values are given in Wt %

Formulations contemplated herein facilitate quick penetration of the active agent with minimum skin sensitivity and/or irritation.

As used herein, "active agent" includes any drug, component or combination thereof, or different salts of any of the active agents (for example naproxen and sodium naproxen) that can be solubilized in either the oil phase and/or organic solvent phase, including drugs and components for human and/or veterinary applications, e.g., NSAIDs, antihistamines, corticosteroids, hydrocortisones, anesthetics, analgesics, opioids, antibiotics, antifungals, Acyclovir, minoxidyl, progesterone, progestogen, and progestogen, estrogen, muscle relaxers, Peptides (Lunasin), Proteins (e.g., botox, insulin, etc.), vitamins, minerals, herbal extracts, cannabidiol, cannabinoids, and the like, as well as mixtures of any two or more different drug categories, or combinations of different drug categories, especially when the combined active oral dosage is less than 30 mg.

Exemplary combinations of active agents include an NSAID and an antihistamine; an NSAID and an opioid; a plurality of antifungals; tramadol and acetaminophen; tenoxicam and bromazepan; fluoxetine and amitriptyline; tizanidine and amitriptyline; gabapentin and amitriptyline; a combination of drugs from the same drug class that differ in their pharmacokinetics (i.e., onset and duration of action), such as a combination of immediate with extended release opioid analgesics; a combination of two or more drugs from different drug classes, such as a combination of an opioid with a tricyclic antidepressant; a combination of drugs delivered through different routes, such as a combination of topical agent (lidocaine or capsaicin) with oral agent (gabapentin); fixed-ratio drug combinations (e.g., short-acting opioid analgesics can be combined with either ibuprofen or acetaminophen (e.g., oxycodone/ibuprofen; tramadol/acetaminophen), analgesics (e.g. menthol, methyl salicylate, aspirin (acetyl salicylate), (all salicylates), capsaicin) and any NSAID; any NSAID and at least one protein; Gabapentin+Lidocaine; Cyclobenzaprine+Naproxen (or any other NSAID); Cyclobenzaprine+Lidocaine; any NSAID (e.g., naproxen or APAP (acetaminophen)) and anesthetic (e.g., Lidocaine or tetracaine); Botox and Lidocaine; antifungal combinations (e.g., Natamycin, Miconazole, Tinacide, Tolnaftate, and/or Lamisil); any NSAID and one or more steroid; magnesium sulfate (Epsom salts)+any NSAID (e.g., naproxen, ibuprufen); choline magnesium salicylate (Trilisate)+lidocaine; APAP (acetaminophen)+anesthetic; Hyaluronic Acid+NSAID; Vitamin A+Vitamin D3+NSAID; copper sulfate+antifungal; and the like, or any multi-drug and multi-component combinations, especially when the active overall oral dosage is less than 30 mg.

For certain active agents, the loading level thereof in formulations contemplated herein may fall in the range of about 0.001 wt % up to about 40 wt %; in certain aspects and embodiments, the loading level of active agent in formulations contemplated herein may fall in the range of about 0.001 wt % up to about 30 wt %; in certain aspects and embodiments, the loading level of active agent in formulations contemplated herein may fall in the range of about 0.001 wt % up to about 20 wt %; in certain aspects and embodiments, the loading level of active agent in formulations contemplated herein may fall in the range of about 0.001 wt % up to about 10 wt %; in certain aspects and embodiments, the loading level of active agent in formulations contemplated herein may fall in the range of about 0.01 wt % up to about 40 wt %; in certain aspects and embodiments, the loading level of active agent in formulations contemplated herein may fall in the range of about 0.01 wt % up to about 30 wt %; in certain aspects and embodiments, the loading level of active agent in formulations contemplated herein may fall in the range of about 0.01 wt % up to about 20 wt %; in certain aspects and embodiments, the loading level of active agent in formulations contemplated herein may fall in the range of about 0.01 wt % up to about 10 wt %; in certain aspects and embodiments, the loading level of active agent in formulations contemplated herein may fall in the range of about 0.1 wt % up to about 40 wt %; in certain aspects and embodiments, the loading level of active agent in formulations contemplated herein may fall in the range of about 0.1 wt % up to about 30 wt %; in certain aspects and embodiments, the loading level of active agent in formulations contemplated herein may fall in the range of about 0.1 wt % up to about 20 wt %; in certain aspects and embodiments, the loading level of active agent in formulations contemplated herein may fall in the range of about 0.1 wt % up to about 10 wt %; in certain aspects and embodiments, the loading level of active agent in formulations contemplated herein may fall in the range of about 1 wt % up to about 40 wt %; in certain aspects and embodiments, the loading level of active agent in formulations contemplated herein may fall in the range of about 1 wt % up to about 30 wt %; in certain aspects and embodiments, the loading level of active agent in formulations contemplated herein may fall in the range of about 1 wt % up to about 20 wt %; in certain aspects and embodiments, the loading level of active agent in formulations contemplated herein may fall in the range of about 1 wt % up to about 10 wt %; in certain aspects and embodiments, the loading level of active agent in formulations contemplated herein may fall in the range of about 5 wt % up to about 40 wt %; in certain aspects and embodiments, the loading level of active agent in formulations contemplated herein may fall in the range of about 5 wt % up to about 30 wt % in certain aspects and embodiments, the loading level of active agent in formulations contemplated herein may fall in the range of about 5 wt % up to about 20 wt %; in certain aspects and embodiments, the loading level of active agent in formulations contemplated herein may fall in the range of about 5 wt % up to about 10 wt %.

As used herein in connection with numerical values, the terms "approximately" and "about" mean+/−10% of the indicated value, including the indicated value.

In certain aspects and embodiments, the active agent employed herein is an NSAID (e.g., flurbiprofen, ibuprofen, naproxen, fenoprofen, pirprofen, carprofen, oxaprozin, tiaprofenic acid, acetylsalicylic acid, diclofenac, diflunisal, etodolac, flufenamic acid, indomethacin, ketorolac, meclofenamate, mefenamic acid, nabumetone, oxyphenbutazone, phenylbutazone, piroxicam, meloxicam, salsalate, sodium salicylate, sulindac, tenoxicam, tolmetin, Rofecoxib (Vioxx), etoricoxib (Arcoxia), celecoxib (Celebrex), valdecoxib (Bextra), and the like).

In certain aspects and embodiments, the active agent employed herein is an antihistamine (e.g., diphenhydramine hydrochloride, chlorpheniramine maleate, and the like).

In certain aspects and embodiments, the active agent employed herein is a steroid, e.g., a corticosteroid (e.g., hydrocortisone, dexamethasone, flumethasone, prednisolone, methylprednisolone, clobetasol propionate, betamethasone benzoate, betamethasone dipropionate, diflorasone diacetate, fluocinonide, mometasone furoate, triamcinolone acetonide, progesterone, progestogen, progestogen, estrogen, and the like).

In certain aspects and embodiments, the active agent employed herein is an anesthetic (e.g., benzocaine, lidocaine, prilocalne, dibucaine, tetracaine, mepivacaine, prilocalne, bupivacaine, and the like).

In certain aspects and embodiments, the active agent employed herein is an analgesic (e.g., glycol salicylate, methyl salicylate, 1-menthol, d,1-camphor, capsaicin, and the like).

In certain aspects and embodiments, the active agent employed herein is an opioid (e.g., morphine, hydromorphone, codeine, fentanyl, and sufentanil, hydrocodone, oxycotin, oxycodon, and the like). The methods and formulations contemplated herein are potentially especially beneficial in the case of opioids, wherein topical delivery thereof may allow for lower doses of the drug to be employed, while still achieving the desired therapeutic effect (e.g., pain relief). Additional benefits to be realized include lowering the opioid drug addiction problem, reducing the symptoms associated with withdrawal, and relieving constipation—all of which are significant side effects of orally administered opioids.

In certain aspects and embodiments, the active agent employed herein is an antibiotic and/or antifungal (e.g., Tetracycline, penicillin, cephalosporin, cyclosporin, Clotrimazole, Metronidizole, Miconazole, Methimazole, and the like).

In certain aspects and embodiments, the active agent employed herein is Acyclovir.

In certain aspects and embodiments, the active agent employed herein is minoxidyl.

In certain aspects and embodiments, the active agent is a vitamin.

In certain aspects and embodiments, the active agent employed herein is a mineral.

In certain aspects and embodiments, the active agent employed herein is an herbal extract or a standardized herbal extract.

In certain aspects and embodiments, the active agent employed herein is a cannabinoid.

In certain aspects and embodiments, the active agent employed herein is a peptide (e.g., Lunasin), or a Protein (e.g., botox, insulin, etc.). A wide variety of proteins are contemplated for use herein, and are particularly useful since delivering proteins and peptides orally is extremely challenging. The very nature of the digestive system is designed to breakdown these polypeptides into amino acids prior to absorption. The low bioavailability of drugs remains to be an active area of research. Several sites in the GIT have been investigated by researchers, but no major breakthrough with broad applicability to diverse proteins and peptides has been achieved.

Protein-based therapeutics contemplated for delivery herein include those which are approved for clinical use in the European Union and/or the USA and include monoclonal antibodies (mAbs), antibody-based drugs, Fc fusion proteins, anticoagulants, blood factors, bone morphogenetic proteins, engineered protein scaffolds, enzymes, growth factors, hormones, interferons, interleukins, thrombolytics, and the like.

In certain aspects and embodiments, the protein-based therapeutic contemplated for delivery herein is a monoclonal antibody (mAb) or an antibody-based drug.

In certain aspects and embodiments, the protein-based therapeutic contemplated for delivery herein is an Fc fusion protein.

In certain aspects and embodiments, the protein-based therapeutic contemplated for delivery herein is an anticoagulant.

In certain aspects and embodiments, the protein-based therapeutic contemplated for delivery herein is a blood factor.

In certain aspects and embodiments, the protein-based therapeutic contemplated for delivery herein is a bone morphogenetic protein.

In certain aspects and embodiments, the protein-based therapeutic contemplated for delivery herein is a engineered protein scaffold.

In certain aspects and embodiments, the protein-based therapeutic contemplated for delivery herein is an enzyme.

In certain aspects and embodiments, the protein-based therapeutic contemplated for delivery herein is a growth factor.

In certain aspects and embodiments, the protein-based therapeutic contemplated for delivery herein is a hormone.

In certain aspects and embodiments, the protein-based therapeutic contemplated for delivery herein is an interferon.

In certain aspects and embodiments, the protein-based therapeutic contemplated for delivery herein is an interleukin.

In certain aspects and embodiments, the protein-based therapeutic contemplated for delivery herein is a thrombolytic.

Protein-based therapeutics contemplated for delivery herein can also be classified based on their molecular mechanism of activity as (a) binding non-covalently to target, e.g., mAbs; (b) affecting covalent bonds, e.g., enzymes; and (c) exerting activity without specific interactions, e.g., serum albumin. Most protein therapeutics currently on the market are recombinant and hundreds of them are in clinical trials for therapy of cancers, immune disorders, infections, and other diseases. New engineered proteins, including bispecific mAbs and multi-specific fusion proteins, mAbs conjugated with small molecule drugs, and proteins with optimized pharmacokinetics, are currently under development. However, in the last several decades, there are no conceptually new methodological developments comparable, e.g., to genetic engineering leading to the development of recombinant therapeutic proteins. It appears that a paradigm change in methodologies and understanding of mechanisms is needed to overcome major challenges, including resistance to therapy, access to targets, complexity of biological systems, and individual variations.

As used herein, "oil" and/or "oil phase" refer to any ingredient that is soluble in an oil, and can include oil soluble actives. The ratio of oil phase/organic solvent phase/actives of 40/40/20+/−20% has been found herein to form a good stable gel. Actives such as NSAIDs (e.g., naproxen, 15% and ibuprofen, 25%) can be employed at fairly high levels. If the oil phase falls below 30% the gel tends to be thin. Exemplary oils or fatty acids contemplated for use herein include Oleic acid, Palmitic acid, Sesame Oil, Caprylic/Capric Triglyceride, Cetyl Alcohol, Cetearyl Alcohol, any vegetable oil or vegetable oil combination where the combination of the fatty acids lauric acid, oleic acid, palmitic acid and ricinoleic acid is greater than 40%, Castor Oil, and the like.

Oils or oil phases contemplated for use herein are typically present in the range of about 15.0 wt %-50.0 wt %; in some embodiments, oils or oil phases contemplated for use herein are present in the range of about 20.0 wt %-40.0 wt %.

In certain aspects and embodiments, the oil phase contemplated for use herein is oleic acid.

In certain aspects and embodiments, the oil phase contemplated for use herein is a sesame oil.

In certain aspects and embodiments, the oil phase contemplated for use herein is a caprylic/capric triglyceride.

In certain aspects and embodiments, the oil phase contemplated for use herein is a cetyl alcohol.

In certain aspects and embodiments, the oil phase contemplated for use herein is a cetearyl alcohol.

In certain aspects and embodiments, the oil phase contemplated for use herein is any vegetable oil or vegetable oil combination where the combination of the fatty acids lauric acid, oleic acid, palmitic acid and ricinoleic acid is greater than 40%.

In certain aspects and embodiments, the oil phase contemplated for use herein is a castor oil.

As used herein, "thickener for oil" and/or "thickener for oil phase", when present in formulations contemplated herein, includes Dibutyl Lauroyl Glutamide, Dibutyl Ethylhexanol Glutamide, Poloxamer 124, Poloxamer 188, Poloxamer 237, Poloxamer 337, Poloxamer 408, Amorphous silica, Polyamide 8, and the like. In certain aspects and embodiments, the oil phase thickener may not be needed and is, therefore optional to form the gel formulation. In certain aspects and embodiments, the polyamide in the solvent phase may be sufficient to form the gel at higher concentration between 10%-20%. This is advantageous in certain aspects and embodiments because the oil phase thickeners Dibutyl Lauroyl Glutamide and Dibutyl Ethylhexanol Glutamide may desirably be avoided as they have not yet been approved for use as pharmaceutical excipients. Since Polyamide 8 is approved for use as a thickener for vegetable oils, it is expected to work in combination with Polyamide 3 for the solvent phase. Accordingly, Polyamide 3 or the Poloxamers may be the only thickener needed for a formulation to form a gel as contemplated herein.

Thickener for oil (and/or thickener for oil phase) contemplated for use herein, when present, is typically present in the range of about 0.5 wt %-15.0 wt %; in some embodiments, thickener for oil is present in the range of about 1.0 wt %-10.0 wt %; in some embodiments, thickener for oil is present in the range of about 2.0 wt %-5.0 wt %.

In certain aspects and embodiments, the thickener for oil phase, when contemplated for use herein, is a dibutyl lauroyl glutamide.

In certain aspects and embodiments, the thickener for oil phase, when contemplated for use herein, is a dibutyl ethylhexanol glutamide.

In certain aspects and embodiments, the thickener for oil phase, when contemplated for use herein, is a Poloxamer 124.

In certain aspects and embodiments, the thickener for oil phase, when contemplated for use herein, is a Poloxamer 188.

In certain aspects and embodiments, the thickener for oil phase, when contemplated for use herein, is a Poloxamer 237.

In certain aspects and embodiments, the thickener for oil phase, when contemplated for use herein, is a Poloxamer 337.

In certain aspects and embodiments, the thickener for oil phase, when contemplated for use herein, is a Poloxamer 408.

In certain aspects and embodiments, the thickener for oil phase, when contemplated for use herein, is a Polyamide 8.

In certain aspects and embodiments, the thickener for oil phase, when contemplated for use herein, is amorphous silica.

As used herein, "organic solvent" includes Dimethyl Sulfoxide (DMSO), Dimethyl Isosorbide (DMI), Dimethyl Formamide (DMF), Ethanol, Ethyl acetate, 1,2-Propanediol, 1,3-Propanediol, Glycerin, and the like.

Organic solvent contemplated for use herein is typically present in the range of about 5.0 wt %-60 wt %; in some embodiments, organic solvent is present in the range of about 15.0 wt %-50 wt %; in some embodiments, organic solvent is present in the range of about 30 wt %-50 wt %; in some embodiments, organic solvent is present in the range of about 20 wt %-40 wt %.

In certain aspects and embodiments, the organic solvent contemplated for use herein is dimethyl sulfoxide (DMSO).

In certain aspects and embodiments, the organic solvent contemplated for use herein is dimethyl formamide (DMF).

In certain aspects and embodiments, the organic solvent contemplated for use herein is dimethyl isosorbide (DMI).

In certain aspects and embodiments, the organic solvent contemplated for use herein is ethanol.

In certain aspects and embodiments, the organic solvent contemplated for use herein is ethyl acetate.

In certain aspects and embodiments, the organic solvent contemplated for use herein is 1,2-propanediol.

In certain aspects and embodiments, the organic solvent contemplated for use herein is 1,3-propanediol.

In certain aspects and embodiments, the organic solvent contemplated for use herein is glycerin.

To aid in keeping the skin hydrated during the application and penetration of formulations for topical application of active(s) contemplated herein, the incorporation of humectants and moisturizers to the solvent phase would be advantageous, making the external layers of the skin (epidermis) softer and more pliable. Humectants and moisturizers contemplated for use herein include ceramides, hyaluronic acid, aloe vera, sodium lactate, lactic acid, sodium PCA (sodium (or zinc) pyroglutamic acid), propylene glycol, hexylene glycol, butylene glycol, glysteryl triacetate, honey, polymeric polyols such as polydextrose and tetralose, urea, sugar alcohols such as glycerol, sorbitol, xylitol and malitol, and the like.

As used herein, "thickener for organic solvent phase" includes Polyamide-2, Polyamide-3, Polyamide-4, Polyamide-6, Polyamide-8, Poloxamer 124, Poloxamer 188, Poloxamer 237, Poloxamer 337, Poloxamer 408, hydroxypropyl cellulose (Klucel, Hercules Aqualon Corp.), hypromellose USP (Methocel E3 Premium LV, Dow Chemical), carbomers (Carbopol, Noveon Corp.), methylcellulose, USP, and the like.

Thickener for organic solvent phase is typically present in the range of about 2.0 wt %-20.0 wt %; in some embodiments, thickener for organic solvent phase is present in the range of about 4.0 wt %-20 wt %; in some embodiments, thickener for organic solvent phase is present in the range of about 8.0 wt %-15 wt %; in some embodiments, thickener for organic solvent phase is present in the range of about 6.0 wt % — 12 wt %.

In certain aspects and embodiments, the thickener for organic solvent phase contemplated for use herein is Polyamide-2.

In certain aspects and embodiments, the thickener for organic solvent phase contemplated for use herein is Polyamide-3.

In certain aspects and embodiments, the thickener for organic solvent phase contemplated for use herein is Polyamide-4.

In certain aspects and embodiments, the thickener for organic solvent phase contemplated for use herein is Polyamide-6.

In certain aspects and embodiments, the thickener for organic solvent phase contemplated for use herein is Polyamide-8.

In certain aspects and embodiments, the thickener for organic solvent phase contemplated for use herein is Poloxamer 124.

In certain aspects and embodiments, the thickener for organic solvent phase contemplated for use herein is Poloxamer 188.

In certain aspects and embodiments, the thickener for organic solvent phase contemplated for use herein is Poloxamer 237.

In certain aspects and embodiments, the thickener for organic solvent phase contemplated for use herein is Poloxamer 337.

In certain aspects and embodiments, the thickener for organic solvent phase contemplated for use herein is Poloxamer 408.

In certain aspects and embodiments, the thickener for organic solvent phase contemplated for use herein is hydroxypropyl cellulose (Klucel, Hercules Aqualon Corp.).

In certain aspects and embodiments, the thickener for organic solvent phase contemplated for use herein is hypromellose USP (Methocel E3 Premium LV, Dow Chemical).

In certain aspects and embodiments, the thickener for organic solvent phase contemplated for use herein is a carbomer (Carbopol, Noveon Corp.).

In certain aspects and embodiments, the thickener for organic solvent phase contemplated for use herein is methylcellulose, USP.

As used herein, "oil and/or solvent soluble skin penetration enhancer" includes High oleic acid canola oil, Olive Oil, Sesame Seed oil, Rice Bran Oil, Palm Oil, Oleic Acid, Squalane, Cetyl Alcohol, Cetearyl Alcohol, Glyceryl Behenate, Glyceryl Monostearate, Castor Oil, Caprylic/Capric Triglyceride, Homosalate, $C_{12-15}$ Alkyl Benzoate, Ceteareth-5, Cocoglycerides, Dibutyl Adipate, Dicapryl Adipate, Dipropylene Glycol Dibenzoate, Isostearyl Alcohol, Lanolin Oil, Laureth-4, Lauryl Alcohol, *Melaleuca* Alternifolia (Tea Tree) Leaf Oil, Menthol-L, Methyl Salicylate, Octocrylene, Oleth-3, PEG-100 Stearate, Polysorbate 20, Polysorbate 80, PPG 425 (PPG-7), Propylene Glycol Isostearate, Sorbitan Oleate, Stearic Acid, Steareth-10, Steareth-2, Stearyl Alcohol, Cetearyl Glucoside, Phosphatidylcholine, Phosphatidylserine, and the like.

While DMSO is recognized in the art as one of the best penetration enhancers, it has some limitations due to skin sensitivities and irritation. The presence of additional components such as high oleic/palmitic fatty acids in the oil phase seems to reduce the occurrence of irritation associated with the use of DMSO. Combinations of DMSO and DMI also seem to minimize the occurrence of skin irritation. DMI is also a good penetration enhancer. Indeed, numerous compounds have been evaluated for penetration enhancing activity, including sulphoxides (such as dimethylsulphoxide, DMSO), Azones (e.g. laurocapram), pyrrolidones (for example 2-pyrrolidone, 2P), alcohols and alkanols (ethanol, or decanol), glycols (for example propylene glycol, PG, a common excipient in topically applied dosage forms), surfactants (also common in dosage forms) and terpenes. Many potential sites and modes of action have been identified for skin penetration enhancers; the intercellular lipid matrix in which the accelerants may disrupt the packing motif, the intracellular keratin domains or through increasing drug partitioning into the tissue by acting as a solvent for the permeant within the membrane. Further potential mechanisms of action, for example with the enhancers acting on desmosomal connections between corneocytes or altering metabolic activity within the skin, or exerting an influence on the thermodynamic activity/solubility of the drug in its vehicle are also feasible.

Oil and/or solvent soluble skin penetration enhancers contemplated for use herein are typically present in the range of about 2.0 wt %-20.0 wt %; in some embodiments, oil and/or solvent soluble skin penetration enhancer is present in the range of about 4.0 wt %-12.0 wt %.

In certain aspects and embodiments, the oil and/or solvent soluble skin penetration enhancer contemplated for use herein is a high oleic acid canola oil.

In certain aspects and embodiments, the oil and/or solvent soluble skin penetration enhancer contemplated for use herein is olive oil.

In certain aspects and embodiments, the oil and/or solvent soluble skin penetration enhancer contemplated for use herein is a sesame seed oil.

In certain aspects and embodiments, the oil and/or solvent soluble skin penetration enhancer contemplated for use herein is a rice bran oil.

In certain aspects and embodiments, the oil and/or solvent soluble skin penetration enhancer contemplated for use herein is a palm oil.

In certain aspects and embodiments, the oil and/or solvent soluble skin penetration enhancer contemplated for use herein is oleic acid.

In certain aspects and embodiments, the oil and/or solvent soluble skin penetration enhancer contemplated for use herein is squalane.

In certain aspects and embodiments, the oil and/or solvent soluble skin penetration enhancer contemplated for use herein is cetyl alcohol.

In certain aspects and embodiments, the oil and/or solvent soluble skin penetration enhancer contemplated for use herein is cetearyl alcohol.

In certain aspects and embodiments, the oil and/or solvent soluble skin penetration enhancer contemplated for use herein is glyceryl behenate.

In certain aspects and embodiments, the oil and/or solvent soluble skin penetration enhancer contemplated for use herein is glyceryl monostearate.

In certain aspects and embodiments, the oil and/or solvent soluble skin penetration enhancer contemplated for use herein is castor oil.

In certain aspects and embodiments, the oil and/or solvent soluble skin penetration enhancer contemplated for use herein is a caprylic/capric triglyceride.

In certain aspects and embodiments, the oil and/or solvent soluble skin penetration enhancer contemplated for use herein is homosalate.

In certain aspects and embodiments, the oil and/or solvent soluble skin penetration enhancer contemplated for use herein is a $C_{12-15}$ alkyl benzoate.

In certain aspects and embodiments, the oil and/or solvent soluble skin penetration enhancer contemplated for use herein is ceteareth-5.

In certain aspects and embodiments, the oil and/or solvent soluble skin penetration enhancer contemplated for use herein is a cocoglyceride.

In certain aspects and embodiments, the oil and/or solvent soluble skin penetration enhancer contemplated for use herein is dibutyl adipate.

In certain aspects and embodiments, the oil and/or solvent soluble skin penetration enhancer contemplated for use herein is dicapryl adipate.

In certain aspects and embodiments, the oil and/or solvent soluble skin penetration enhancer contemplated for use herein is dipropylene glycol dibenzoate.

In certain aspects and embodiments, the oil and/or solvent soluble skin penetration enhancer contemplated for use herein is isostearyl alcohol.

In certain aspects and embodiments, the oil and/or solvent soluble skin penetration enhancer contemplated for use herein is lanolin oil.

In certain aspects and embodiments, the oil and/or solvent soluble skin penetration enhancer contemplated for use herein is laureth-4.

In certain aspects and embodiments, the oil and/or solvent soluble skin penetration enhancer contemplated for use herein is lauryl alcohol.

In certain aspects and embodiments, the oil and/or solvent soluble skin penetration enhancer contemplated for use herein is *Melaleuca* Alternifolia (Tea Tree) leaf oil, Orange oil, Lemon Oil or any other essential fragrant oil containing terpenes (e.g., d-Limonene, myrcene, linalool, and the like), and the like.

In certain aspects and embodiments, the oil and/or solvent soluble skin penetration enhancer contemplated for use herein is menthol-L.

In certain aspects and embodiments, the oil and/or solvent soluble skin penetration enhancer contemplated for use herein is methyl salicylate.

In certain aspects and embodiments, the oil and/or solvent soluble skin penetration enhancer contemplated for use herein is octocrylene.

In certain aspects and embodiments, the oil and/or solvent soluble skin penetration enhancer contemplated for use herein is oleth-3.

In certain aspects and embodiments, the oil and/or solvent soluble skin penetration enhancer contemplated for use herein is PEG-100 stearate.

In certain aspects and embodiments, the oil and/or solvent soluble skin penetration enhancer contemplated for use herein is Polysorbate 20.

In certain aspects and embodiments, the oil and/or solvent soluble skin penetration enhancer contemplated for use herein is Polysorbate 80.

In certain aspects and embodiments, the oil and/or solvent soluble skin penetration enhancer contemplated for use herein is PPG 425 (PPG-7).

In certain aspects and embodiments, the oil and/or solvent soluble skin penetration enhancer contemplated for use herein is propylene glycol isostearate.

In certain aspects and embodiments, the oil and/or solvent soluble skin penetration enhancer contemplated for use herein is sorbitan oleate.

In certain aspects and embodiments, the oil and/or solvent soluble skin penetration enhancer contemplated for use herein is stearic acid.

In certain aspects and embodiments, the oil and/or solvent soluble skin penetration enhancer contemplated for use herein is steareth-10.

In certain aspects and embodiments, the oil and/or solvent soluble skin penetration enhancer contemplated for use herein is steareth-2.

In certain aspects and embodiments, the oil and/or solvent soluble skin penetration enhancer contemplated for use herein is stearyl alcohol.

In certain aspects and embodiments, the oil and/or solvent soluble skin penetration enhancer contemplated for use herein is cetearyl glucoside.

In certain aspects and embodiments, the oil and/or solvent soluble skin penetration enhancer contemplated for use herein is phosphatidylcholine.

In certain aspects and embodiments, the oil and/or solvent soluble skin penetration enhancer contemplated for use herein is phosphatidylserine.

The preceding skin penetration enhancers are oil phase ingredients that are also soluble in the organic solvent phase, and help to minimize skin irritation and sensitivity.

A vegetable oil (in an oil phase high in oleic and palmitic fatty acids) is miscible in the organic solvent phase which may include DMSO, DMI, DMF and/or ethanol (DMSO, DMF and DMI are good penetration enhancers, ethanol is a good solvent soluble in DMSO, DMF and DMI). The other oil phase ingredients are chosen for their solubility in polyamide polymers. In some embodiments, the oil thickeners employed herein are dibutyl lauroyl glutamide and dibutyl ethylhexanol glutamide (available from Ajinamoto), Polyamide 8, and the like. Such agents can thicken the oil phase ingredients at low concentrations and, at the same time, are soluble in the organic solvent phase. These polymers are particularly effective for thickening oils. As known in the art, for oil-in-water or water-in-oil emulsions, emulsifiers are used to bind the oil phase and water phase. For the oil in organic solvent "emulsions" the cross solubilities are used to keep the two phases together, otherwise the two layers will separate.

Kraton G styrene-ethylene-propylene (SEP) polymers with a di-block structure, Kraton ethylene/propylene (EP) star polymers, Kraton G styrene-ethylene-butylene-styrene (SEBS) polymers, and the like, are thickeners for the organic solvent phase. Kraton A polymers have a unique midblock structure compatible with natural, polar, and ester oils, and can be used as thickeners for the oil phase.

Exemplary pharmaceutical excipients that will work in the oil phase and are penetration enhancers (and are available commercially from Gatefosse) include: PEG-8 beeswax, Propylene glycol monocaprylate, Propylene glycol monocaprylate, Glycerol dibehenate, Glyceryl behenate, Mixture of Cetyl alcohol and ethoxylated fatty alcohols (Ceteth-20, Steareth-20), Mono & digly cerides, Glycerol monostearate, Mono and diglycerides, Mixture of Glycerol monostearate (and) stearate, Medium-chain triglycerides, Medium chain fatty acid triglyceride, Propylene glycol dicaprylate/dicaprate, Oleoyl macrogol-6 glycerides, Oleoyl polyoxyl-6 glycerides, Linoleoyl macrogol-6 glycerides, polyoxyl-6 glycerides, Lauroyl macrogol-6 glycerides, Lauroyl polyoxyl-6 glycerides, Caprylocaproyl macrogol-8 glycerides, Caprylocaproyl polyoxyl-8 glycerides, Propylene glycol monolaurate, Propylene glycol monolaurate, Propylene glycol monopalmitostearate, Triglycerol diisostearate, Polyglyceryl-3-diisostearate, Polyglyceryl-3 dioleate, and the like, as well as mixtures of any two or more thereof.

In certain aspects and embodiments, the pharmaceutical excipient that will work in the oil phase contemplated for use herein is phosphatidylcholine, which can be used in a formulation to incorporate a third liposomal phase. Secondary or other actives can be dissolved and surrounded by small spheres called liposomes or incorporated into multilayer liposomes. This third liposomal phase is typically added to a formulation after the "oil-in-organic solvent" gel structure has formed below 60° C.

In certain aspects and embodiments, the pharmaceutical excipient that will work in the oil phase contemplated for use herein is PEG-8 beeswax.

In certain aspects and embodiments, the pharmaceutical excipient that will work in the oil phase contemplated for use herein is Propylene glycol monocaprylate.

In certain aspects and embodiments, the pharmaceutical excipient that will work in the oil phase contemplated for use herein is Propylene glycol monocaprylate.

In certain aspects and embodiments, the pharmaceutical excipient that will work in the oil phase contemplated for use herein is Glycerol dibehenate.

In certain aspects and embodiments, the pharmaceutical excipient that will work in the oil phase contemplated for use herein is Glyceryl behenate.

In certain aspects and embodiments, the pharmaceutical excipient that will work in the oil phase contemplated for use herein is Mixture of Cetyl alcohol and ethoxylated fatty alcohols (Ceteth-20, Steareth-20).

In certain aspects and embodiments, the pharmaceutical excipient that will work in the oil phase contemplated for use herein is Mono & diglycerides.

In certain aspects and embodiments, the pharmaceutical excipient that will work in the oil phase contemplated for use herein is Glycerol monostearate.

In certain aspects and embodiments, the pharmaceutical excipient that will work in the oil phase contemplated for use herein is Mono and diglycerides.

In certain aspects and embodiments, the pharmaceutical excipient that will work in the oil phase contemplated for use herein is Mixture of Glycerol monostearate (and) stearate.

In certain aspects and embodiments, the pharmaceutical excipient that will work in the oil phase contemplated for use herein is Medium-chain triglycerides.

In certain aspects and embodiments, the pharmaceutical excipient that will work in the oil phase contemplated for use herein is Medium chain fatty acid triglyceride.

In certain aspects and embodiments, the pharmaceutical excipient that will work in the oil phase contemplated for use herein is Propylene glycol dicaprylate/dicaprate.

In certain aspects and embodiments, the pharmaceutical excipient that will work in the oil phase contemplated for use herein is Oleoyl macrogol-6 glycerides.

In certain aspects and embodiments, the pharmaceutical excipient that will work in the oil phase contemplated for use herein is Oleoyl polyoxyl-6 glycerides.

In certain aspects and embodiments, the pharmaceutical excipient that will work in the oil phase contemplated for use herein is Linoleoyl macrogol-6 glycerides.

In certain aspects and embodiments, the pharmaceutical excipient that will work in the oil phase contemplated for use herein is polyoxyl-6 glycerides.

In certain aspects and embodiments, the pharmaceutical excipient that will work in the oil phase contemplated for use herein is Lauroyl macrogol-6 glycerides.

In certain aspects and embodiments, the pharmaceutical excipient that will work in the oil phase contemplated for use herein is Lauroyl polyoxyl-6 glycerides.

In certain aspects and embodiments, the pharmaceutical excipient that will work in the oil phase contemplated for use herein is Caprylocaproyl macrogol-8 glycerides.

In certain aspects and embodiments, the pharmaceutical excipient that will work in the oil phase contemplated for use herein is Caprylocaproyl polyoxyl-8 glycerides.

In certain aspects and embodiments, the pharmaceutical excipient that will work in the oil phase contemplated for use herein is Propylene glycol monolaurate.

In certain aspects and embodiments, the pharmaceutical excipient that will work in the oil phase contemplated for use herein is Propylene glycol monolaurate.

In certain aspects and embodiments, the pharmaceutical excipient that will work in the oil phase contemplated for use herein is Propylene glycol monopalmitostearate.

In certain aspects and embodiments, the pharmaceutical excipient that will work in the oil phase contemplated for use herein is Triglycerol diisostearate.

In certain aspects and embodiments, the pharmaceutical excipient that will work in the oil phase contemplated for use herein is Polyglyceryl-3-diisostearate.

In certain aspects and embodiments, the pharmaceutical excipient that will work in the oil phase contemplated for use herein is Polyglyceryl-3 dioleate.

In certain embodiments of the present disclosure, <10 wt % water is present in the formulations contemplated herein; in certain embodiments, <1 wt % water is present. The amount of water could potentially determine the rate at which a drug or other component is delivered through the skin. With no water or minimal water, penetration of the active occurs rapidly. As the water concentration increases, the rate of delivery of the active decreases. DMSO is less effective as a penetration enhancer as the DMSO/Water balance changes.

As used herein, "thixotropic or heat thinning gel" refers to a stable gel formed by solubilizing the polymers in the oil and organic solvent phases at a temperature in the range of about 70-130° C., then combining the two phases and allowing the gel to cool; wherein said gel has the ability to rapidly liquefy upon exposure to heat and/or shear, e.g., by application to the skin and/or nails of a subject in need thereof.

As used herein, "quick" penetration of the active agent refers to the time required for delivery of an active agent to a local site, typically 60 minutes or less.

As used herein, "minimum skin irritation" refers to the degree of irritation experienced by a subject to whom formulations/emulsions/gels according to the present disclosure are applied, as measured, for example, by redness in the area of application, dermatitis or itching in the area of application, etc.

In accordance with another embodiment of the present disclosure, there are provided gels comprising oil and organic solvent, said gel comprising:
  (a) at least one active agent;
  (b) an oil phase and optionally a thickener therefor;
  (c) a continuous organic solvent phase and a thickener therefor; and
wherein:
  (d) an oil and/or solvent soluble skin penetration enhancer;
  said gels comprise <10 wt % water; and
  said gel is optionally a thixotropic or heat thinning gel.

The resulting gel facilitates quick penetration of the active agent with minimum skin and/or nail sensitivity and/or irritation.

In accordance with yet another embodiment of the present disclosure, there are also provided methods for the topical delivery of an active agent to a subject in need thereof, said method comprising topically applying a gel as described herein to a subject in need thereof.

In accordance with yet another embodiment of the present disclosure, there are provided methods for preparing a gel comprising oil and organic solvent, said methods comprising combining:
  (a) at least one active agent;
  (b) an oil, and optionally a thickener therefor;
  (c) an organic solvent, and a thickener therefor; and
  (d) an oil and/or solvent soluble skin penetration enhancer;
  under conditions suitable for the formation of a gel.

An exemplary protocol for creating viable oil-in-organic solvent gels for transdermal delivery includes the following steps:
  (1) Choose any oil phase ingredient(s) or combination thereof that is miscible or soluble with the solvent phase ingredient(s). See list of "oil phase agents";
  (2) Choose polymer(s) or combinations thereof at appropriate concentrations which when heated to a temperature <120° C. are soluble in the oil phase. See list of "oil phase thickening agents";
  (3) Choose polymer(s) or combinations thereof at appropriate concentrations which when heated to a temperature <100° C. are soluble in the solvent phase. See list of "organic solvent phase thickening agents";
  (4) Choose active(s) at appropriate dosage(s) or combinations thereof which when added to the oil phase and/or the organic solvent phase are soluble in the oil and/or organic solvent phase when the temperature is <80° C. See "active agents";
  (5) The active(s) may also be solublized in a third or liposomal phase at a temperature <80° C. The liposomal phase includes phosphatidylcholine.
  (6) The oil phase is added to the organic solvent phase at a temperature <80° C., and/or a liposomal phase is added after the oil phase is added to the organic solvent phase at a temperature <60° C. The mixture forms a transparent, semi-transparent or opaque solution which when cooled to room temperature forms a viscous gel. The gel can be thixotropic which has quick transdermal delivery properties of the active(s) typically within 60 minutes.

Any drug or nutraceutical category of active(s) with solubility in the oil and/or organic solvent and/or liposomal phases >/=10% by weight, or >/=20 mg/0.2 grams of gel are possible. Indeed, any drug or nutraceutical (whether expressly set forth herein) can be delivered by the methods described herein so long as the concentration of active(s) are <10% by weight and forms a stable gel.

In accordance with still another embodiment of the present disclosure, there are provided gels for topical delivery of an active agent to a subject in need thereof, said gels comprising:
(a) at least one active agent;
(b) an oil phase, and optionally a thickener therefor;
(c) an organic solvent, and a thickener therefor; and
(d) an oil and/or solvent soluble skin penetration enhancer;
wherein:
said gel comprises <10 wt % water; and
said gel optionally forms a thixotropic thinning gel.

The resulting gel facilitates quick penetration of the active agent with minimum skin and/or nail sensitivity and/or irritation.

In accordance with another embodiment of the present disclosure, there are provided methods for the topical delivery of an active agent to a subject in need thereof, said method comprising topically applying a gel as described herein to the skin and/or nails of a subject in need thereof.

The term "treating" refers to preventing a disease, disorder or condition from occurring in a cell, a tissue, a system, animal or human which may be predisposed to the disease, disorder and/or condition but has not yet been diagnosed as having it; stabilizing a disease, disorder or condition, i.e., arresting its development; and/or relieving one or more symptoms of the disease, disorder or condition, i.e., causing regression of the disease, disorder and/or condition.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

DETAILED DESCRIPTION OF THE PREFERRED EMBODIMENTS

In accordance with certain aspects and embodiments of the present disclosure, there are provided formulations wherein:
the active agent employed herein is at least one NSAID;
the oil phase contemplated for use herein is oleic acid and/or palmitic acid, or a high oleic acid/palmitic acid vegetable oil and/or a castor oil;
the thickener for oil phase contemplated for use herein is a dibutyl lauroyl glutamide;
the organic solvent contemplated for use herein is dimethyl sulfoxide (DMSO), dimethyl formamide (DMF) and/or dimethyl isosorbide (DMI);
the thickener for organic solvent phase contemplated for use herein is a Polyamide or a Poloxamer (e.g., Polyamide-2, Polyamide-3, Polyamide-4, Polyamide-6, Polyamide-8, and the like);
the oil and/or solvent soluble skin penetration enhancer contemplated for use herein is Caprylic/Capric Triglyceride; and optionally
the pharmaceutical excipient that will work in the oil phase contemplated for use herein is phosphatidylcholine or menthol.

In accordance with certain aspects and embodiments of the present disclosure, there are provided formulations wherein:
the active agent employed herein is at least one opioid;
the oil phase contemplated for use herein is oleic acid and/or palmitic acid, or a high oleic acid/palmitic acid vegetable oil, or castor oil;
the thickener for oil phase contemplated for use herein is optional, but when present is dibutyl lauroyl glutamide;
the organic solvent contemplated for use herein is dimethyl sulfoxide (DMSO) and/or dimethyl isosorbide (DMI) or any combination thereof;
the thickener for organic solvent phase contemplated for use herein is a Polyamide or Poloxamer (e.g., Polyamide-2, Polyamide-3, Polyamide-4, Polyamide-6, Polyamide-8, and the like);
the oil and/or solvent soluble skin penetration enhancer contemplated for use herein is Caprylic/Capric Triglyceride; and optionally
the pharmaceutical excipient that will work in the oil phase contemplated for use herein is phosphatidylcholine or menthol.

The following examples are provided to further illustrate aspects of the present disclosure. These examples are non-limiting and should not be construed as limiting any aspect of the disclosure.

Example 1

Preparation of Exemplary Formulations for Topical Application of Active(s)

Numerous exemplary formulations as contemplated herein are summarized in Table 2 below, and are prepared as follows:
A. Weigh and mix OIL PHASE ingredients, heat until dissolved up to 100° C.;
B. Weigh, mix and heat SOLVENT PHASE ingredients to 75° C.-80° C. or until all SOLVENT PHASE ingredients dissolve;
C. Maintain temperature at 65° C. Add Active to solution (B), mix until dissolved;
D. Add (A) oil phase mixture to (C) solvent phase mixture with active, keep mixing at low RPM until gel forms;
Cool mixture to RT and package.

TABLE 2

| | Formulation* | | | | | | | | |
|---|---|---|---|---|---|---|---|---|---|
| | 1A | 1B | 1C | 1D | 1E | 1F | 1G | 1H | 1I |
| Oil Phase Ingredients | | | | | | | | | |
| Sesame oil | 0 | 0 | 0 | 23.0 | 0 | 5.0 | 0 | 23.0 | 0 |
| Oleic Acid | 0 | 0 | 20.0 | 0 | 0 | 0 | 0 | 0 | 0 |
| Palmitic Acid | 0 | 0 | 0 | 0 | 0 | 0 | 0 | 0 | 0 |

TABLE 2-continued

|  | Formulation* | | | | | | | | |
|---|---|---|---|---|---|---|---|---|---|
|  | 1A | 1B | 1C | 1D | 1E | 1F | 1G | 1H | 1I |
| Menthol | 2.0 | 0 | 0 | 0 | 2.0 | 2.0 | 2.0 | 0 | 2.0 |
| Wintergreen oil | 1.0 | 0 | 0 | 0 | 1.0 | 1.0 | 1.0 | 0 | 1.0 |
| Olive oil | 8.0 | 25.0 | 0 | 0 | 6.0 | 0 | 6.0 | 0 | 8.0 |
| Castor oil | 1.0 | 0 | 0 | 0 | 0 | 1.0 | 1.0 | 0 | 1.0 |
| Cetyl Alcohol | 3.0 | 0 | 0 | 0 | 2.0 | 3.0 | 3.0 | 0 | 3.0 |
| Cetearyl Alcohol | 3.0 | 0 | 0 | 0 | 2.0 | 3.0 | 3.0 | 0 | 0 |
| Median Chain Triglyceride | 8.0 | 15.0 | 10.0 | 12.0 | 4.0 | 6.0 | 0 | 12.0 | 8.0 |
| Squalane | 0 | 0 | 0 | 0 | 0 | 0 | 0 | 0 | 0 |
| Glyceryl Layrate | 0 | 0 | 0 | 0 | 0 | 0 | 0 | 0 | 0 |
| Cetearyl Glucoside | 0 | 0 | 0 | 0 | 0 | 0 | 5.0 | 0 | 3.0 |
| Dibutyl Lauroyl Glutamide | 2.0 | 3.0 | 0 | 0 | 0 | 2.0 | 0 | 0 | 2.0 |
| Dibutyl Ethylhexanol Glutamide | 0 | 0 | 0 | 0 | 0 | 0 | 2.0 | 0 | 0 |
| Polyamide 8 | 0 | 0 | 0 | 0 | 0 | 0 | 0 | 0 | 0 |
| Polyamide-3 | 0 | 0 | 0 | 0 | 0 | 0 | 0 | 0 | 0 |
| Poloxamer 108 | 0 | 0 | 0 | 0 | 6.0 | 0 | 0 | 0 | 0 |
| Poloxamer 408 | 0 | 0 | 6.0 | 10.0 | 0 | 0 | 10.0 | 10.0 | 0 |
| Solvent Phase Ingredients | | | | | | | | | |
| DMSO | 35.0 | 0 | 0 | 18.0 | 30.0 | 30.0 | 0 | 19.0 | 26.0 |
| DMI | 0 | 22.0 | 5.0 | 0 | 15.0 | 8.0 | 0 | 0 | 0 |
| DMF | 0 | 0 | 24.0 | 0 | 0 | 0 | 20.0 | 0 | 0 |
| Water | 0 | 0 | 0 | 0 | 0 | 0 | 0 | 0 | 0 |
| 1,2-Propanediol | 0 | 0 | 0 | 1.0 | 0.5 | 0 | 0 | 0 | 1.0 |
| Ethanol | 10.0 | 0 | 0 | 0 | 0 | 0 | 6.0 | 0 | 0 |
| Glycerin | 0 | 0 | 0 | 0 | 0 | 0 | 0 | 0 | 0 |
| Polyamide 3 | 10.0 | 10.0 | 0 | 0 | 0 | 8.0 | 8.0 | 0 | 10.0 |
| Poly(1-vinyl-2-pyrrolidinone), PVP | 1.0 | 0 | 0 | 0 | 0 | 0 | 0 | 0 | 0 |
| Poloxamer 108 | 0 | 0 | 0 | 0 | 16.0 | 0 | 2.0 | 0 | 0 |
| Polomamer 408 | 0 | 0 | 10.0 | 10.0 | 0 | 0 | 0 | 10.0 | 0 |
| Phophatdyl choline | 1.0 | 0 | 0 | 1.0 | 0.5 | 1.0 | 1.0 | 1.0 | 10.0 |
| Actives | | | | | | | | | |
| Naproxen | 15.0 | 0 | 0 | 0 | 15.0 | 0 | 0 | 0 | 0 |
| Ibuprofen | 0 | 25.0 | 25.0 | 25.0 | 0 | 0 | 30.0 | 25.0 | 0 |
| Acetaminophen | 0 | 0 | 0 | 0 | 0 | 30.0 | 0 | 0 | 0 |
| Lidocaine | 0 | 0 | 0 | 0 | 0 | 0 | 0 | 0 | 0 |
| Acyclovir | 0 | 0 | 0 | 0 | 0 | 0 | 0 | 0 | 0 |
| Dichlofenac sodium | 0 | 0 | 0 | 0 | 0 | 0 | 0 | 0 | 0 |
| R-Lipoic acid | 0 | 0 | 0 | 0 | 0 | 0 | 0 | 0 | 25.0 |
| Tetracaine | 0 | 0 | 0 | 0 | 0 | 0 | 0 | 0 | 0 |
| Tetracycline | 0 | 0 | 0 | 0 | 0 | 0 | 0 | 0 | 0 |
| Vitamin B12 cyanocobalamin | 0 | 0 | 0 | 0 | 0 | 0 | 0 | 0 | 0 |
| TOTAL | 100 | 100 | 100 | 100 | 100 | 100 | 100 | 100 | 100 |

*All values are given in Wt %

Example 2

Preparation of Additional Exemplary Formulations

Additional exemplary formulations as contemplated herein are prepared as described above, and are summarized in Table 3 below.

TABLE 3

|  | Formulation* | | | | | | | |
|---|---|---|---|---|---|---|---|---|
|  | 2A | 2B | 2C | 2D | 2E | 2F | 2G | 2H |
| Oil Phase Ingredients | | | | | | | | |
| Sesame oil | 0 | 0 | 0 | 0 | 0 | 5.0 | 0 | 0 |
| Oleic Acid | 0 | 15.0 | 20.0 | 23.0 | 0 | 0 | 0 | 13.0 |
| Palmitic Acid | 0 | 10.0 | 0 | 0 | 0 | 0 | 0 | 10.0 |
| Menthol | 2.0 | 0 | 0 | 0 | 2.0 | 2.0 | 2.0 | 0 |
| Wintergreen oil | 1.0 | 0 | 0 | 0 | 1.0 | 1.0 | 1.0 | 0 |
| Olive oil | 8.0 | 0 | 0 | 0 | 6.0 | 0 | 6.0 | 0 |
| Castor oil | 1.0 | 0 | 0 | 0 | 0 | 1.0 | 1.0 | 0 |
| Cetyl Alcohol | 3.0 | 0 | 0 | 0 | 2.0 | 3.0 | 3.0 | 0 |

TABLE 3-continued

|  | Formulation* | | | | | | | |
|---|---|---|---|---|---|---|---|---|
|  | 2A | 2B | 2C | 2D | 2E | 2F | 2G | 2H |
| Cetearyl Alcohol | 3.0 | 0 | 0 | 0 | 2.0 | 3.0 | 3.0 | 0 |
| Median Chain Triglyceride | 8.0 | 15.0 | 10.0 | 12.0 | 4.0 | 6.0 | 0 | 12.0 |
| Squalane | 0 | 0 | 0 | 0 | 0 | 0 | 0 | 0 |
| Glyceryl Layrate | 0 | 0 | 0 | 0 | 0 | 0 | 0 | 0 |
| Cetearyl Glucoside | 0 | 0 | 0 | 0 | 0 | 0 | 5.0 | 0 |
| Dibutyl Lauroyl Glutamide | 2.0 | 0 | 0 | 0 | 0 | 2.0 | 0 | 0 |
| Dibutyl Ethylhexanol Glutamide | 0 | 3.0 | 0 | 0 | 0 | 0 | 2.0 | 0 |
| Polyamide 8 | 0 | 0 | 0 | 0 | 0 | 0 | 0 | 0 |
| Polyamide-3 | 0 | 0 | 0 | 0 | 0 | 0 | 0 | 0 |
| Poloxamer 108 | 0 | 0 | 0 | 0 | 6.0 | 0 | 0 | 0 |
| Poloxamer 408 | 0 | 0 | 6.0 | 10.0 | 0 | 0 | 6.0 | 10.0 |
| Solvent Phase Ingredients | | | | | | | | |
| DMSO | 35.0 | 22.0 | 24.0 | 18.0 | 30.0 | 30.0 | 24.0 | 19.0 |
| DMI | 0 | 0 | 5.0 | 0 | 15.0 | 8.0 | 0 | 0 |
| DMF | 0 | 0 | 0 | 0 | 0 | 0 | 0 | 0 |
| Water | 0 | 0 | 0 | 0 | 0 | 0 | 0 | 0 |
| 1,2-Propanediol | 0 | 0 | 0 | 1.0 | 0.5 | 0 | 0 | 0 |
| Ethanol | 10.0 | 0 | 0 | 0 | 0 | 0 | 6.0 | 0 |
| Ethyl acetate | 0 | 0 | 0 | 0 | 0 | 0 | 0 | 0 |
| Glycerin | 0 | 0 | 0 | 0 | 0 | 0 | 0 | 0 |
| 1,3-Propanediol | 0 | 0 | 0 | 0 | 0 | 0 | 0 | 0 |
| Polyamide 3 | 10.0 | 10.0 | 0 | 0 | 0 | 8.0 | 8.0 | 0 |
| Poly(1-vinyl-2-pyrrolidinone), PVP | 1.0 | 0 | 0 | 0 | 0 | 0 | 0 | 0 |
| Poloxamer 108 | 0 | 0 | 0 | 0 | 16.0 | 0 | 2.0 | 0 |
| Polomamer 408 | 0 | 0 | 10.0 | 10.0 | 0 | 0 | 0 | 10.0 |
| Phophatdyl choline | 1.0 | 0 | 0 | 1.0 | 0.5 | 1.0 | 1.0 | 1.0 |
| Actives | | | | | | | | |
| Naproxen | 15.0 | 0 | 0 | 0 | 15.0 | 0 | 0 | 0 |
| Ibuprofen | 0 | 25.0 | 25.0 | 25.0 | 0 | 0 | 30.0 | 25.0 |
| Acetaminophen | 0 | 0 | 0 | 0 | 0 | 30.0 | 0 | 0 |
| Lidocaine | 0 | 0 | 0 | 0 | 0 | 0 | 0 | 0 |
| Acyclovir | 0 | 0 | 0 | 0 | 0 | 0 | 0 | 0 |
| Dichlofenac sodium | 0 | 0 | 0 | 0 | 0 | 0 | 0 | 0 |
| Cyclosporin | 0 | 0 | 0 | 0 | 0 | 0 | 0 | 0 |
| R-Lipoic acid | 0 | 0 | 0 | 0 | 0 | 0 | 0 | 0 |
| Guaifensin | 0 | 0 | 0 | 0 | 0 | 0 | 0 | 0 |
| Tetracaine | 0 | 0 | 0 | 0 | 0 | 0 | 0 | 0 |
| Vitamin B12 cyanocobalamin | 0 | 0 | 0 | 0 | 0 | 0 | 0 | 0 |
| TOTAL | 100 | 100 | 100 | 100 | 100 | 100 | 100 | 100 |

*All values are given in Wt %

Example 3

Preparation of Additional Exemplary Formulations

Additional exemplary formulations as contemplated herein are prepared as described above, and are summarized in Table 4 below.

TABLE 4

|  | Formulation* | | | | | | | | |
|---|---|---|---|---|---|---|---|---|---|
|  | 3A | 3B | 3C | 3D | 3E | 3F | 3G | 3H | 3I |
| Oil Phase Ingredients | | | | | | | | | |
| Sesame oil | 0 | 7.0 | 0 | 0 | 0 | 0 | 0 | 0 | 0 |
| Oleic Acid | 12.0 | 0 | 7.0 | 7.0 | 14.0 | 0 | 0 | 13.0 | 20.0 |
| Palmitic Acid | 8.0 | 7.0 | 0 | 0 | 11.0 | 0 | 0 | 10.0 | 5.0 |
| Menthol | 0 | 0 | 0 | 0 | 0 | 2.0 | 2.0 | 0 | 3.0 |
| Wintergreen oil | 0 | 0 | 0 | 0 | 0 | 1.0 | 1.0 | 0 | 0 |
| Olive oil | 0 | 0 | 0 | 0 | 0 | 10.4 | 6.0 | 0 | 0 |
| Castor oil | 0 | 0 | 0 | 0 | 0 | 1.0 | 1.0 | 0 | 0 |
| Cetyl Alcohol | 0 | 0 | 0 | 0 | 0 | 4.0 | 3.0 | 0 | 0 |
| Cetearyl Alcohol | 0 | 0 | 0 | 0 | 0 | 4.0 | 3.0 | 0 | 0 |
| Median Chain Triglyceride | 10.0 | 7.0 | 0 | 0 | 5.0 | 10.0 | 10.0 | 12.0 | 5.0 |

TABLE 4-continued

|  | Formulation* | | | | | | | | |
|---|---|---|---|---|---|---|---|---|---|
|  | 3A | 3B | 3C | 3D | 3E | 3F | 3G | 3H | 3I |
| Squalane | 0 | 0 | 0 | 0 | 0 | 0 | 0 | 0 | 0 |
| Glyceryl Layrate | 0 | 0 | 0 | 0 | 0 | 0 | 0 | 0 | 0 |
| Cetearyl Glucoside | 0 | 0 | 0 | 0 | 0 | 0 | 0 | 0 | 0 |
| Dibutyl Lauroyl Glutamide | 2.5 | 0 | 0 | 0 | 2.5 | 2.0 | 0 | 3.0 | 2.5 |
| Dibutyl Ethylhexanol Glutamide | 0 | 2.5 | 0 | 0 | 0 | 0 | 2.0 | 0 | 0 |
| Polyamide 8 | 0 | 0 | 0 | 0 | 0 | 0 | 0 | 0 | 0 |
| Polyamide-3 | 0 | 0 | 0 | 0 | 0 | 0 | 0 | 0 | 0 |
| Poloxamer 108 | 0 | 0 | 0 | 0 | 0 | 0 | 0 | 0 | 0 |
| Poloxamer 408 | 0 | 0 | 0 | 0 | 0 | 0 | 0 | 0 | 0 |
| Vitamin D3, 1.0M IU/gm | 0 | 0 | 0 | 0 | 0 | 0 | 1.0 | 0 | 0 |
| Urea | 0 | 0 | 9.0 | 9.0 | 0 | 0 | 0 | 0 | 0 |
| Boswellia serrata, 90% | 0 | 0 | 0 | 0 | 1.0 | 0 | 0 | 0 | 0 |
| Solvent Phase Ingredients | | | | | | | | | |
| DMSO | 31.1 | 39.5 | 44.0 | 42.0 | 42.1 | 39.595 | 37.0 | 32.8 | 35.0 |
| DMI | 0 | 0 | 0 | 12.0 | 0 | 13.0 | 13.0 | 0 | 0 |
| DMF | 0 | 0 | 0 | 0 | 0 | 0 | 0 | 0 | 0 |
| Water | 0 | 0 | 0 | 0 | 0 | 0 | 0 | 0 | 0 |
| 1,2-Propanediol | 0 | 0 | 12.0 | 0 | 3.0 | 1.5 | 2.5 | 2.00 | 0 |
| Ethanol | 10.0 | 0 | 0 | 0 | 0 | 0 | 6.0 | 10.0 | 0 |
| Ethyl acetate | 0 | 0 | 0 | 0 | 0 | 0 | 0 | 0 | 0 |
| Glycerin | 0 | 0 | 0 | 0 | 0 | 0 | 0 | 0 | 0 |
| 1,3-Propanediol | 0 | 0 | 0 | 0 | 0 | 0 | 0 | 0 | 0 |
| Polyamide 3 | 10.0 | 0 | 0 | 0 | 10.0 | 10.0 | 10.0 | 0 | 10.0 |
| Poly(1-vinyl-2-pyrrolidinone), PVP | 0 | 10.0 | 8.0 | 0 | 0 | 0 | 0 | 0 | 0 |
| Poloxamer 108 | 0 | 0 | 0 | 0 | 0 | 0 | 0 | 0 | 0 |
| Polomamer 408 | 0 | 0 | 0 | 10.0 | 0 | 0 | 0 | 10.0 | 0 |
| Phophatdyl choline | 0 | 0 | 0 | 0 | 3.0 | 1.5 | 2.5 | 2.0 | 0 |
| Aloe | 0.2 | 0 | 0 | 0 | 0 | 0 | 0 | 0.2 | 0.2 |
| Urea | 8.0 | 8.0 | 0 | 0 | 8.0 | 0 | 0 | 0 | 5.3 |
| Actives | | | | | | | | | |
| Naproxen | 0 | 15.0 | 15.0 | 15.0 | 0 | 0 | 0 | 0 | 0 |
| Ibuprofen | 0 | 0 | 0 | 0 | 0 | 0 | 0 | 0 | 0 |
| Acetaminophen | 0 | 0 | 0 | 0 | 0 | 0 | 0 | 0 | 0 |
| Lidocaine | 4.0 | 4.0 | 5.0 | 5.0 | 0 | 0 | 0 | 0 | 7.0 |
| Acyclovir | 0 | 0 | 0 | 0 | 0 | 0 | 0 | 5.0 | 0 |
| Betamethasone dipropionate | 0 | 0 | 0 | 0 | 0 | 0 | 0 | 0 | 0 |
| Dichlofenac sodium | 4.2 | 0 | 0 | 0 | 0 | 0 | 0 | 0 | 0 |
| Cyclosporin | 0 | 0 | 0 | 0 | 0 | 0 | 0 | 0 | 0 |
| R-Lipoic acid | 0 | 0 | 0 | 0 | 0 | 0 | 0 | 0 | 0 |
| Guaifensin | 0 | 0 | 0 | 0 | 0 | 0 | 0 | 0 | 0 |
| Tetracaine | 0 | 0 | 0 | 0 | 0 | 0 | 0 | 0 | 7.0 |
| Tetracycline | 0 | 0 | 0 | 0 | 0 | 0 | 0 | 0 | 0 |
| Vitamin B12 cyanocobalamin | 0 | 0 | 0 | 0 | 0 | 0.005 | 0 | 0 | 0 |
| Cannabinoids, 99% | 0 | 0 | 0 | 0 | 0.4 | 0 | 0 | 0 | 0 |
| TOTAL | 100 | 100 | 100 | 100 | 100 | 100 | 100 | 100 | 100 |

*All values are given in Wt %

Example 4

Preparation of Additional Exemplary Formulations

Additional exemplary formulations as contemplated herein are prepared as described above, and are summarized in Table 5 below.

TABLE 5

|  | Formulation* | | | | | | | |
|---|---|---|---|---|---|---|---|---|
|  | 4A | 4B | 4C | 4D | 4E | 4F | 4G | 4H |
| Oil Phase Ingredients | | | | | | | | |
| Sesame oil | 0 | 7.0 | 0 | 0 | 0 | 0 | 0 | 0 |
| Oleic Acid | 12.0 | 0 | 12.0 | 0 | 0 | 10.0 | 7.0 | 16.0 |
| Palmitic Acid | 8.0 | 7.0 | 8.0 | 0 | 0 | 0 | 0 | 11.0 |
| Menthol | 0 | 0 | 0 | 3.0 | 0 | 2.0 | 0 | 0 |

TABLE 5-continued

| | 4A | 4B | 4C | 4D | 4E | 4F | 4G | 4H |
|---|---|---|---|---|---|---|---|---|
| Wintergreen oil | 0 | 0 | 0 | 0 | 1.0 | 1.0 | 0 | 0 |
| Olive oil | 0 | 0 | 0 | 0 | 0 | 0 | 0 | 0 |
| Castor oil | 0 | 0 | 0 | 0 | 0 | 1.0 | 0 | 0 |
| Cetyl Alcohol | 0 | 0 | 0 | 0 | 0 | 4.0 | 0 | 0 |
| Cetearyl Alcohol | 0 | 0 | 0 | 4.0 | 0 | 4.0 | 0 | 0 |
| Median Chain Triglyceride | 0 | 0 | 10.0 | 25.0 | 19.0 | 10.0 | 0 | 0 |
| Squalane | 10.0 | 7.0 | 0 | 6.0 | 4.0 | 0 | 0 | 0 |
| Glyceryl Layrate | 0 | 0 | 0 | 2.0 | 0 | 0 | 0 | 0 |
| Cetearyl Glucoside | 0 | 0 | 0 | 4.0 | 0 | 0 | 0 | 0 |
| Dibutyl Lauroyl Glutamide | 2.5 | 0 | 2.5 | 1.0 | 2.0 | 2.0 | 0 | 2.0 |
| Dibutyl Ethylhexanol Glutamide | 0 | 1.0 | 0 | 1.0 | 1.0 | 0 | 0 | 0 |
| Polyamide 8 | 0 | 5.0 | 0 | 0 | 0 | 0 | 0 | 0 |
| Polyamide-3 | 0 | 0 | 0 | 0 | 0 | 0 | 0 | 0 |
| Poloxamer 108 | 0 | 0 | 0 | 0 | 5.0 | 0 | 0 | 0 |
| Poloxamer 408 | 0 | 0 | 0 | 0 | 0 | 0 | 0 | 0 |
| Vitamin D3, 1.0M IU/gm | 0 | 0 | 0 | 0 | 0 | 2.0 | 0 | 0 |
| Urea | 0 | 0 | 8.0 | 0 | 0 | 0 | 8.0 | 0 |
| Boswellia serrata, 90% | 0 | 0 | 0 | 0 | 0 | 0 | 0 | 0 |
| Solvent Phase Ingredients | | | | | | | | |
| DMSO | 34.3 | 26.0 | 30.1 | 25.0 | 31.0 | 30.0 | 42.0 | 44.0 |
| DMI | 0 | 10.0 | 0 | 9.0 | 11.0 | 21.0 | 5.0 | 0 |
| DMF | 0 | 0 | 0 | 0 | 0 | 0 | 0 | 0 |
| Water | 2.0 | 0 | 0 | 0 | 0 | 0 | 0 | 0 |
| 1,2-Propanediol | 0 | 0 | 3.0 | 1.5 | 3.0 | 1.5 | 0 | 3.0 |
| Ethanol | 10.0 | 0 | 0 | 0 | 0 | 0 | 0 | 0 |
| Ethyl acetate | 0 | 0 | 0 | 0 | 0 | 0 | 0 | 0 |
| Glycerin | 0 | 0 | 0 | 2.0 | 1.0 | 0 | 0 | 1.0 |
| 1,3-Propanediol | 0 | 0 | 0 | 0 | 1.0 | 0 | 0 | 0 |
| Polyamide 3 | 10.0 | 0 | 10.0 | 0 | 5.0 | 10.0 | 0 | 10.0 |
| Poly(1-vinyl-2-pyrrolidinone), PVP | 0 | 0 | 0 | 0 | 0 | 0 | 0 | 0 |
| Poloxamer 108 | 0 | 0 | 0 | 0 | 0 | 0 | 0 | 0 |
| Polomamer 408 | 0 | 10.0 | 0 | 0 | 0 | 0 | 18.0 | 0 |
| Phophatdyl choline | 0 | 0 | 0 | 1.5 | 1.0 | 1.5 | 0 | 3.0 |
| Aloe | 0.2 | 0 | 0.2 | 0 | 0 | 0 | 0 | 0 |
| Urea | 8.0 | 8.0 | 8.0 | 0 | 0 | 0 | 0 | 8.0 |
| Actives | | | | | | | | |
| Naproxen | 0 | 15.0 | 0 | 15.0 | 15.0 | 0 | 15.0 | 0 |
| Ibuprofen | 0 | 0 | 0 | 0 | 0 | 0 | 0 | 0 |
| Acetaminophen | 0 | 0 | 0 | 0 | 0 | 0 | 0 | 0 |
| Lidocaine | 0 | 4.0 | 4.0 | 0 | 0 | 0 | 5.0 | 0 |
| Acyclovir | 0 | 0 | 0 | 0 | 0 | 0 | 0 | 0 |
| Dichlofenac sodium | 0 | 0 | 4.2 | 0 | 0 | 0 | 0 | 0 |
| R-Lipoic acid | 0 | 0 | 0 | 0 | 0 | 0 | 0 | 0 |
| Tetracaine | 3.0 | 0 | 0 | 0 | 0 | 0 | 0 | 0 |
| Vitamin B12 cyanocobalamin | 0 | 0 | 0 | 0 | 0 | 0 | 0 | 0 |
| Cannabinoids, 99% | 0 | 0 | 0 | 0 | 0 | 0 | 0 | 2.0 |
| TOTAL | 100 | 100 | 100 | 100 | 100 | 100 | 100 | 100 |

*All values are given in Wt %

Example 5

Case Study of 15% Naproxen Gel and 30% Acetaminophen Gel

The use of all topical gels was done with physician oversight and the informed consent of the subject.

For the Naproxen Pain Gel, 15 wt % (see Formulation 1A in Table 2 above), one pump from an airless container equals 0.4 grams, which contains 60 mg of Naproxen.

For the Acetaminophen Pain Gel, 30 wt % (see Formulation 1F in Table 2 above), one pump from an airless container equals 0.4 grams, which contains 120 mg of Acetaminophen.

Details Regarding Topical Application of Naproxen
  Subject: Male, 59 yr. old.
  Localized Topical Application Area: Groin, right hip area
  Use Frequency: Morning and bedtime
  Dosage: One pump, 0.4 grams, 60 mg Naproxen
  Duration of pain relief: 10-12 hours
  Pain level before application: 7 (scale 1-10 worst)
  Pain level after application: 2 (scale 1-10 worst)
  Time to effectiveness: 30 to 60 minutes
  Side effects: none Details Regarding Topical Application of Acetaminophen
  Localized Topical Application Area: Groin, right hip area
  Use Frequency: Morning and bedtime
  Dosage: One pump, 0.4 grams, 120 mg Acetaminophen.
  Duration of pain relief: 0
  Pain level before application: 7 (scale 1-10 worst)
  Pain level after application: 7 (scale 1-10 worst)
  Side effects: none The subject was seen by an orthopedic specialist due to decreased mobility and range of motion in the hip joint. Physical therapy and Celebrex were ordered as a precursor to future hip surgery.

The Celebrex was initiated and stopped after 3 days due to drowsiness and GI side effects. No other oral or topical products were used or taken for hip discomfort—including opioids, analgesics, and topical pain relievers.

The subject is in continuous discomfort due to intense physical labor at work.

The subject started on 15 wt % Naproxen gel, 0.4 grams (60 mg of Naproxen), before work and at bedtime for 2 days, and felt a reduction on the pain scale from 7 down to 2 after 2 applications of the gel. Pain was much improved over the course of the therapy; and the subject was able to perform activities at work with pain relief. Continued use has allowed the subject to use only 60 mg twice a day of the 15% Naproxen Gel to maintain significant pain relief.

After 1 full day of not using the naproxen gel, the subject began using the 30% Acetominophen gel by applying 1 full pump of the acetaminophen gel (0.4 gm or 120 mg of Acetaminophen) from an airless container. The gel was applied once in the morning before work, and again at bedtime. Prior to application, the pain level was at a 7 (on a scale of 1-10, with zero being no pain). The pain level remained at 7 after application. The subject felt little relief after applying the acetaminophen gel. The pain continued throughout the day at a 7 level. After 2 days of using the acetaminophen gel with little pain relief, the acetaminophen gel was discontinued and the use of the naproxen gel was reinstated. Using the 15% naproxen gel, pain relief was controlled at a 2 level during the course of naproxen gel therapy.

This example demonstrates that the formulations contemplated herein are useful for topical delivery of actives such as the NSAID naproxen.

Example 6

Case Study of Vitamin B12 Gel

The use of all topical gels was done with physician oversight and the informed consent of the subject.

A topical Vitamin B12 formula containing 200 mcg of methyl cobalamin per pump of 200 mg (see Formulation 3F in Table 4) was applied to the thighs of a test subject once in the morning and once in the evening. The subject's blood was analyzed for Vitamin B12 and recorded a blood concentration of 278 pg/ml. The topical Vitamin B12 gel formulation was applied for 14 days and the Vitamin B12 blood concentration was recorded as 441 pg/ml. The test subject followed his normal daily routine with no other supplements taken and no changes to his normal diet.

The invention illustratively described herein may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The contents of the articles, patents, and patent applications, and all other documents and electronically available information mentioned or cited herein, are hereby incorporated by reference in their entirety to the same extent as if each individual publication was specifically and individually indicated to be incorporated by reference. Applicants reserve the right to physically incorporate into this application any and all materials and information from any such articles, patents, patent applications, or other documents.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the inventions embodied therein herein disclosed may be resorted to by those skilled in the art, and that such modifications and variations are considered to be within the scope of this invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

Other embodiments are set forth within the following claims.

What is claimed is:

1. A method for the topical delivery of diclofenac to a subject in need thereof, comprising:
   topically applying a non-aqueous transparent gel formulation to the subject, the non-aqueous transparent gel formulation comprising
   (a) diclofenac;
   (b) oleic acid;
   (c) at least one organic solvent selected from the group consisting of dimethyl isosorbide, dimethyl formamide, ethanol, ethyl acetate, 1,2-propanediol, 1,3-propanediol, and glycerin;
   (d) dimethylsulfoxide; and
   (e) hydroxypropyl cellulose.

2. The method of claim 1, wherein the non-aqueous transparent gel formulation further comprises 2.0 wt % to 5.0 wt % of at least one compound selected from the group consisting of Dibutyl Lauroyl Glutamide, Dibutyl Ethylhexanol Glutamide, Poloxamer 124, Poloxamer 188, Poloxamer 237, Poloxamer 337, Poloxamer 408, and Polyamide 8.

3. The method of claim 1, wherein component (c) of the non-aqueous transparent gel formulation comprises ethanol and the combined concentration of dimethylsulfoxide and component (c) in the formulation is 30 wt % to 60 wt %.

4. The method of claim 2, wherein component (c) of the non-aqueous transparent gel formulation comprises ethanol and the combined concentration of dimethylsulfoxide and component (c) in the formulation is 30 wt % to 60 wt %.

5. The method of claim 1, wherein the at least one organic solvent comprises 1,2-propanediol.

6. The method of claim 2, wherein the at least one organic solvent comprises 1,2-propanediol.

7. The method of claim 1, wherein component (a) of the non-aqueous transparent gel formulation comprises 1-10 wt % diclofenac or a salt thereof.

8. The method of claim 2, wherein component (a) of the non-aqueous transparent gel formulation comprises 1-10 wt % diclofenac or a salt thereof.

9. The method of claim 3, wherein component (a) of the non-aqueous transparent gel formulation comprises 1-10 wt % diclofenac or a salt thereof.

10. The method of claim 4, wherein component (a) of the non-aqueous transparent gel formulation comprises 1-10 wt % diclofenac or a salt thereof.

11. The method of claim 5, wherein component (a) of the non-aqueous transparent gel formulation comprises 1-10 wt % diclofenac or a salt thereof.

12. The method of claim 6, wherein component (a) of the non-aqueous transparent gel formulation comprises 1-10 wt % diclofenac or a salt thereof.

13. A method for the topical delivery of diclofenac to a subject in need thereof, comprising:
topically applying a non-aqueous transparent gel formulation to the subject, the non-aqueous transparent gel formulation comprising
(a) diclofenac or a salt thereof;
(b) oleic acid;
(c) ethanol
(d) hydroxypropyl cellulose;
(e) propylene glycol; and
(f) dimethylsulfoxide,
wherein said non-aqueous transparent gel formulation comprises 2-5 wt % hydroxypropyl cellulose, 1-10 wt % diclofenac or a salt thereof, and a combined concentration of dimethylsulfoxide and ethanol of 30-60 wt %.

* * * * *